(12) United States Patent
Whittaker et al.

(10) Patent No.: US 8,147,481 B2
(45) Date of Patent: Apr. 3, 2012

(54) VASCULAR GUIDEWIRE CONTROL APPARATUS

(75) Inventors: David R. Whittaker, Potomac, MD (US); Allison M. Whittaker, Potomac, MD (US); Keith E. Lauritzen, Gig Harbor, WA (US); Steven Dibdin, Bloomfield, NJ (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1397 days.

(21) Appl. No.: 11/621,536

(22) Filed: Jan. 9, 2007

(65) Prior Publication Data

US 2007/0179472 A1 Aug. 2, 2007

Related U.S. Application Data

(63) Continuation-in-part of application No. 11/090,574, filed on Mar. 24, 2005, now Pat. No. 7,615,032, and a continuation-in-part of application No. 11/090,588, filed on Mar. 24, 2005, now abandoned.

(60) Provisional application No. 60/757,443, filed on Jan. 9, 2006, provisional application No. 60/760,511, filed on Jan. 21, 2006.

(51) Int. Cl.
*A61M 25/16* (2006.01)

(52) U.S. Cl. ........ 604/533; 604/159; 604/171; 604/535; 600/585

(58) Field of Classification Search .................. 604/528, 604/159, 95.04, 171, 533, 535; 600/434, 600/585, 433; 606/129
See application file for complete search history.

(56) References Cited

U.S. PATENT DOCUMENTS

| 5,137,288 A | 8/1992 | Starkey et al. |
| 5,161,534 A | 11/1992 | Berthiaume |
| 5,238,005 A | 8/1993 | Imran |
| 5,392,778 A | 2/1995 | Horzewski |
| 5,415,633 A | 5/1995 | Lazarus et al. |
| 5,443,078 A | 8/1995 | Uflacker |
| 5,480,382 A | 1/1996 | Hammerslag et al. |
| 5,492,131 A | 2/1996 | Galel |

(Continued)

FOREIGN PATENT DOCUMENTS

EP 0 310 295 4/1989

(Continued)

OTHER PUBLICATIONS

Patents Abstract of Japan, JP 5177002, Noriyasu et al., Published Jul. 20, 1993.

(Continued)

*Primary Examiner* — Laura Bouchelle
(74) *Attorney, Agent, or Firm* — Tarolli, Sundheim, Covell & Tummino LLP

(57) ABSTRACT

A controller for use with a guidewire, such as a vascular guidewire, provides a mechanism for gripping and applying a torque to the guidewire without the need to thread the guidewire axially through the controller and at a location close to a point of access of the guidewire. In one embodiment, the controller includes a side-access, multi-part assembly including a collet or other gripping element that applies a uniform radially inward force on the guidewire. In another embodiment, for use with guidewires having active electrically controllable elements, the controller integrally or removably incorporates a switch or other mechanism to initiate an energized state. The controller thereby permits ergonomic, single-handed control of an electronically steerable guidewire, including axially displacing, torquing and steering the guidewire.

16 Claims, 14 Drawing Sheets

U.S. PATENT DOCUMENTS

| | | | |
|---|---|---|---|
| 5,636,642 A | 6/1997 | Palermo | |
| 5,771,902 A | 6/1998 | Lee et al. | |
| 5,851,189 A | 12/1998 | Forber | |
| 5,906,590 A | 5/1999 | Hunjan et al. | |
| 5,916,147 A | 6/1999 | Boury | |
| 6,033,414 A * | 3/2000 | Tockman et al. | 606/129 |
| 6,231,563 B1 | 5/2001 | White et al. | |
| 6,352,515 B1 | 3/2002 | Anderson et al. | |
| 6,500,130 B2 | 12/2002 | Kinsella et al. | |
| 6,502,606 B2 | 1/2003 | Klin | |
| 6,514,237 B1 | 2/2003 | Maseda | |
| 6,533,772 B1 | 3/2003 | Sherts et al. | |
| 6,551,302 B1 | 4/2003 | Rosinko et al. | |
| 6,579,246 B2 | 6/2003 | Jacobsen et al. | |
| 6,579,279 B1 | 6/2003 | Rabiner et al. | |
| 6,616,628 B2 | 9/2003 | Hayzelden | |
| 2001/0039412 A1 | 11/2001 | Fariabi | |
| 2002/0013550 A1 | 1/2002 | Unsworth et al. | |
| 2002/0072689 A1 | 6/2002 | Klint | |
| 2002/0082523 A1 | 6/2002 | Kinsella et al. | |
| 2003/0078645 A1 | 4/2003 | Pigott | |
| 2003/0097080 A1 | 5/2003 | Esashi et al. | |
| 2003/0181827 A1 | 9/2003 | Hojeibane et al. | |
| 2003/0199818 A1 | 10/2003 | Waldhauser et al. | |
| 2003/0208219 A1 | 11/2003 | Aznoian et al. | |
| 2004/0133185 A1 * | 7/2004 | Nash et al. | 604/533 |

FOREIGN PATENT DOCUMENTS

| | | |
|---|---|---|
| EP | 0 383 914 | 8/1990 |
| EP | 0 543 539 | 5/1993 |
| WO | WO 90/03760 | 4/1990 |
| WO | WO 93/25267 | 12/1993 |
| WO | WO 96/13206 | 5/1996 |
| WO | WO 02/083010 | 10/2002 |
| WO | WO 2004/000107 A2 | 12/2004 |
| WO | WO 2004/000107 A3 | 12/2004 |

OTHER PUBLICATIONS

Patents Abstract of Japan, JP 1198564, Hirose, Published Aug. 10, 1989.

International Search Report and Written Opinion for PCT/US05/010208, dated Jul. 25, 2005.

International Search Report and Written Opinion for PCT/US05/010207, dated Oct. 17, 2005.

International Search Report and Written Opinion for PCT/US05/010198, dated Jul. 25, 2005.

* cited by examiner

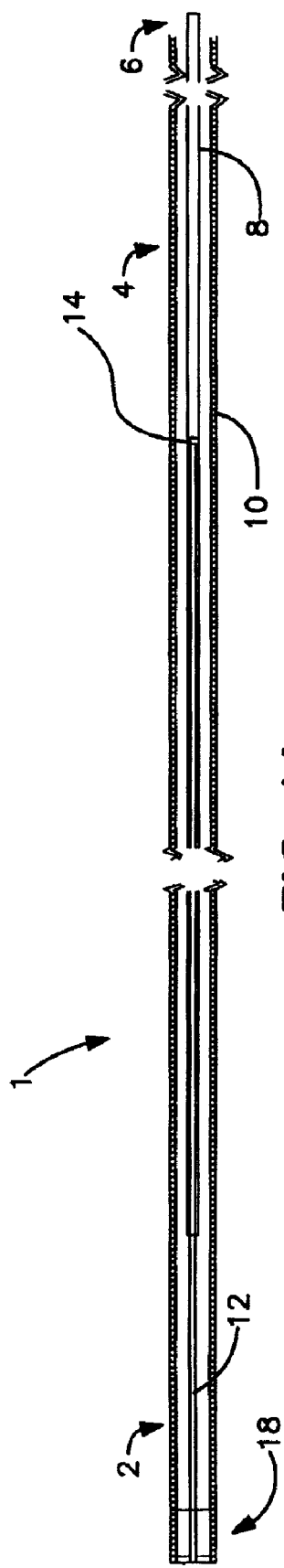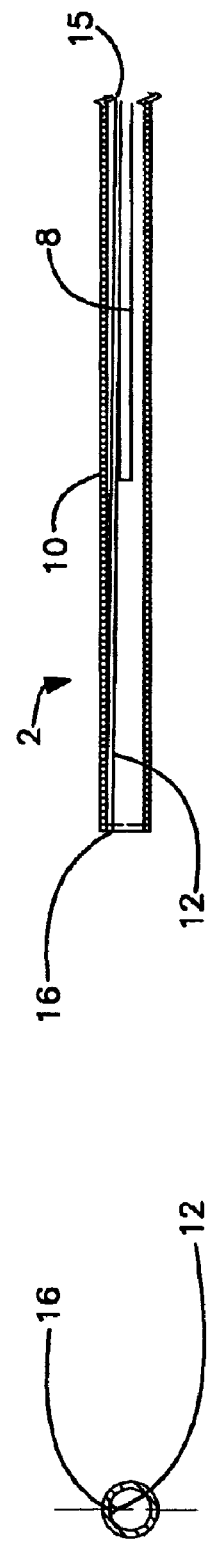

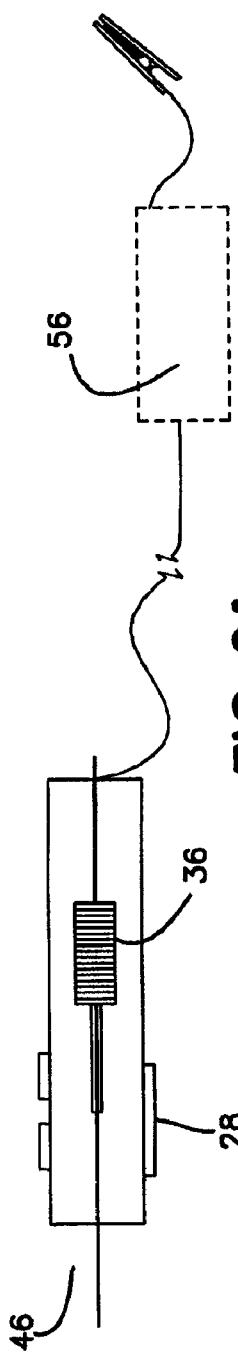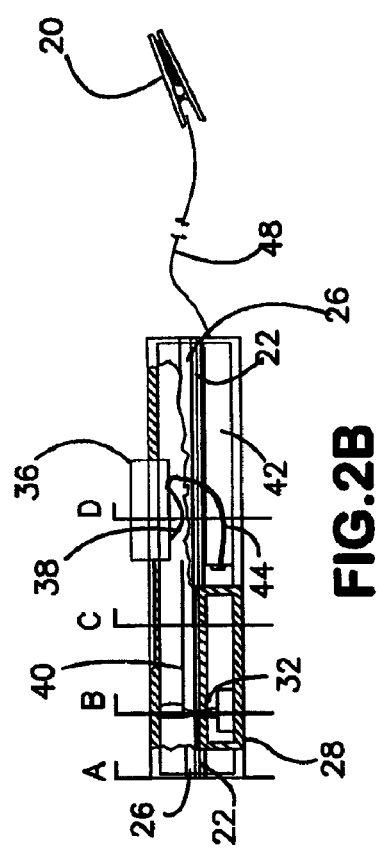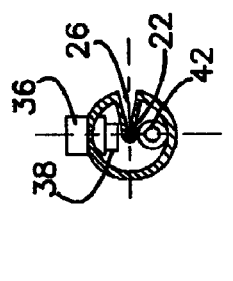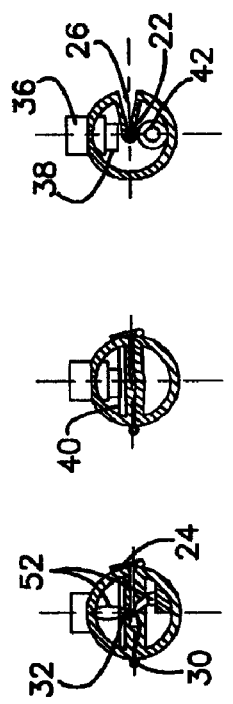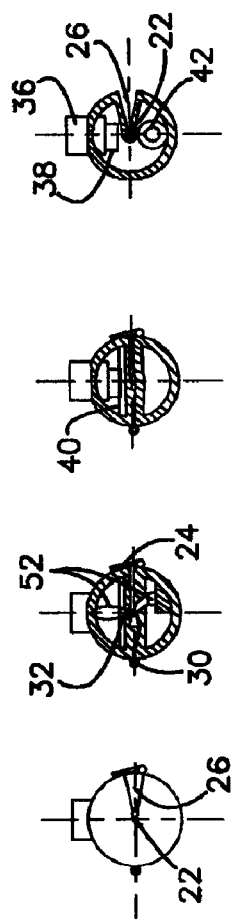

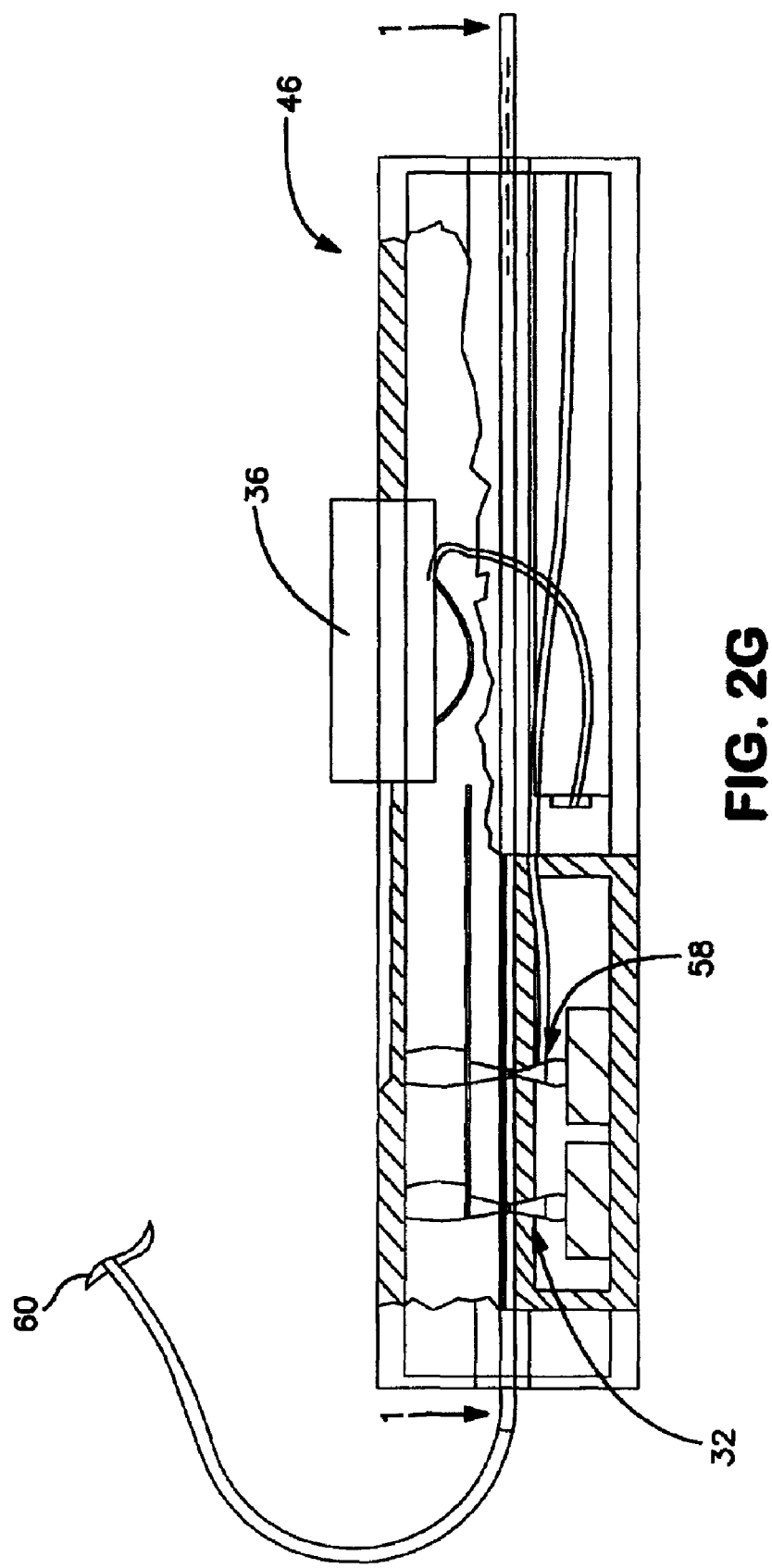

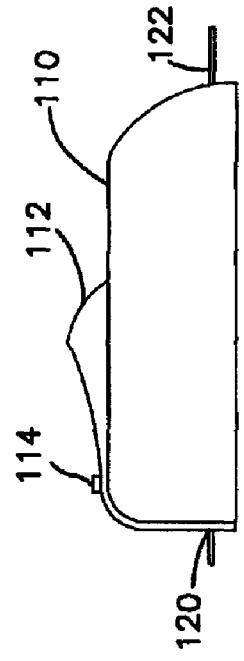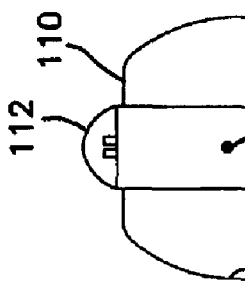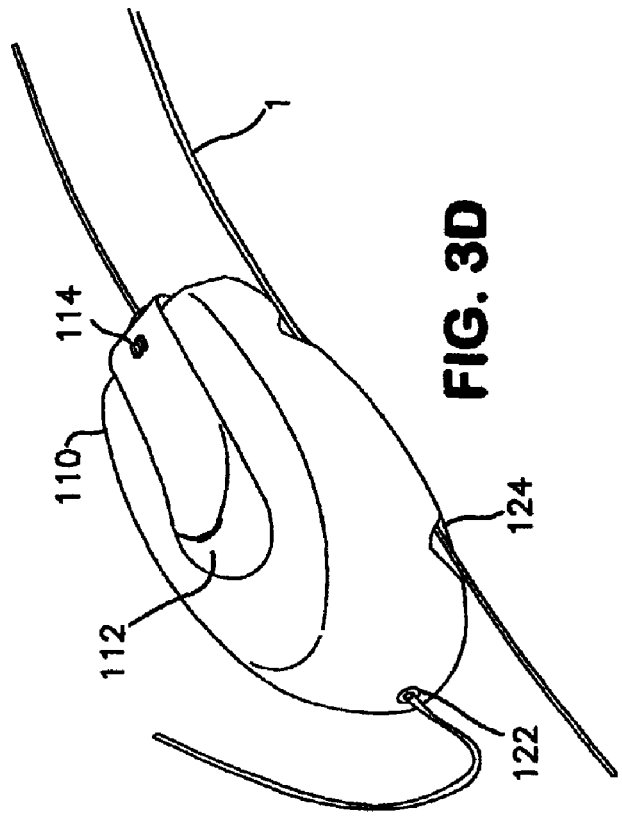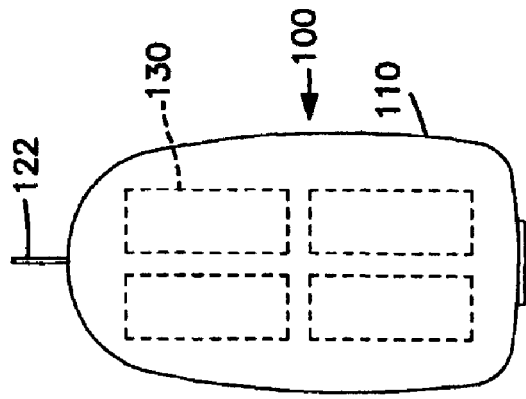

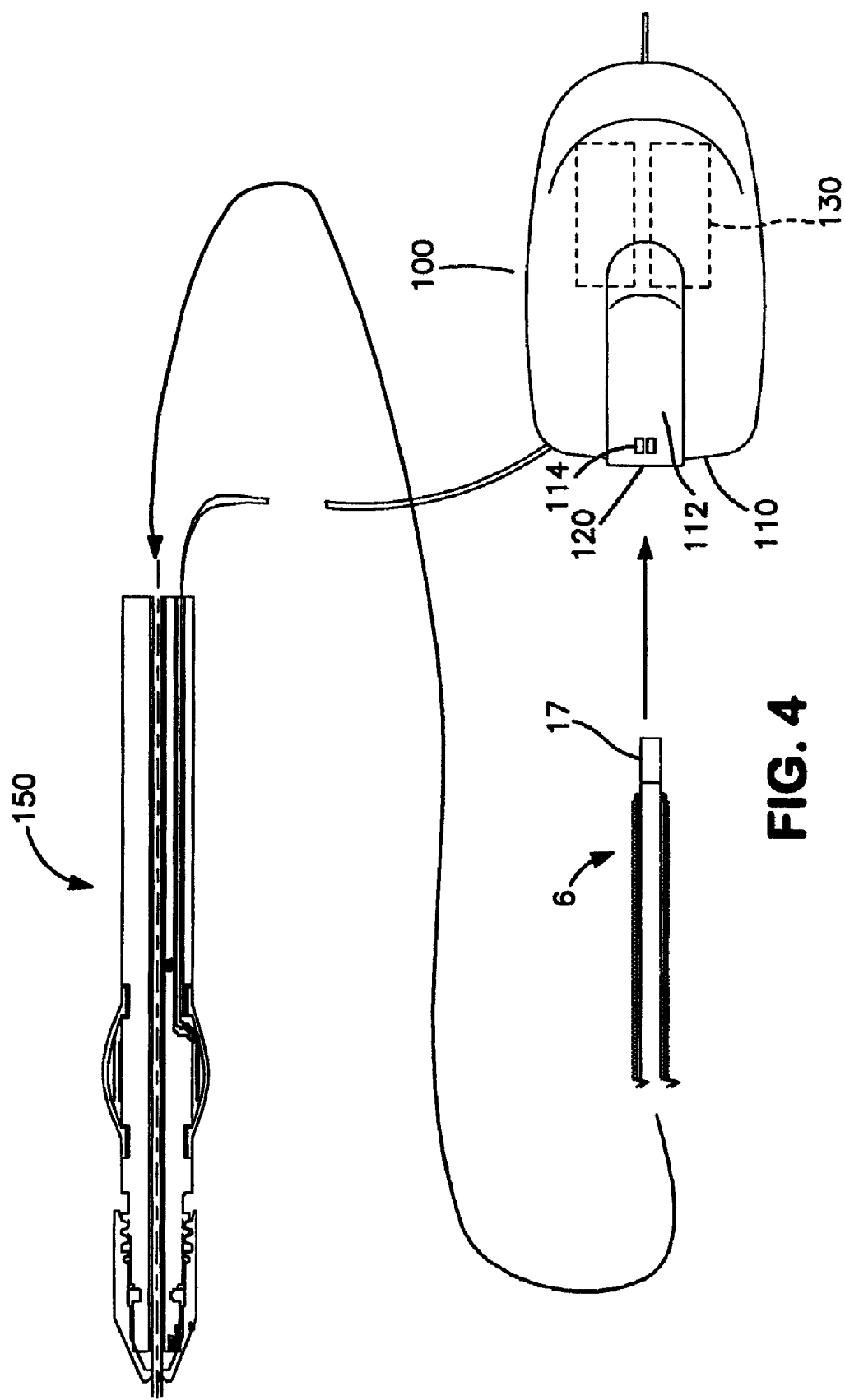

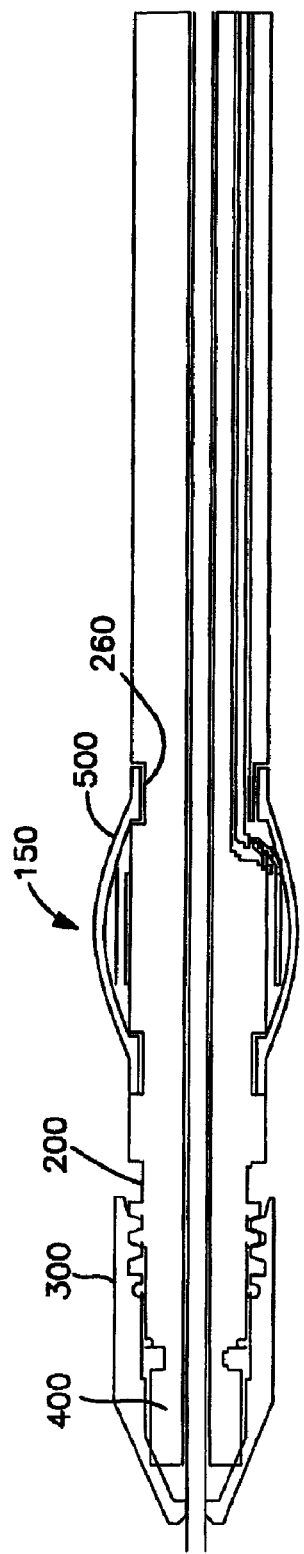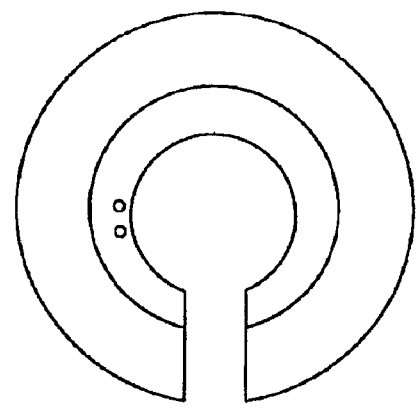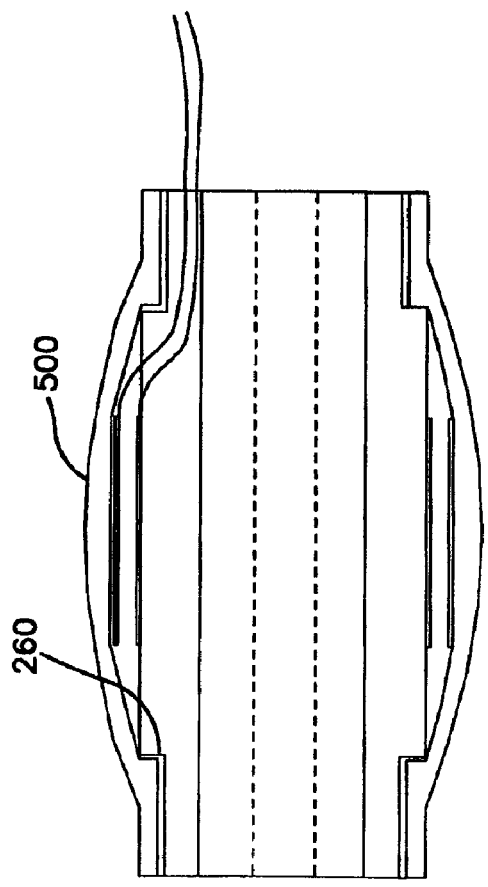
FIG. 5A
FIG. 5C
FIG. 5B

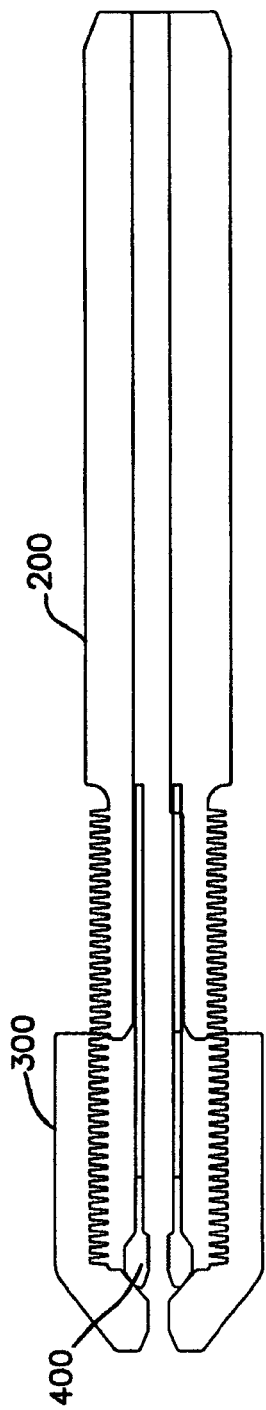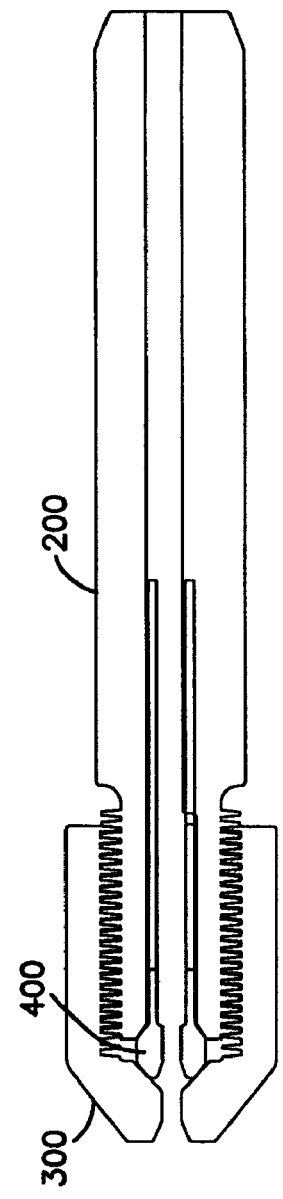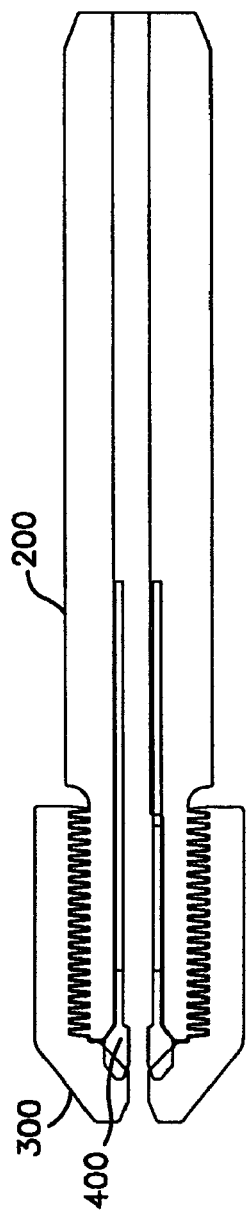

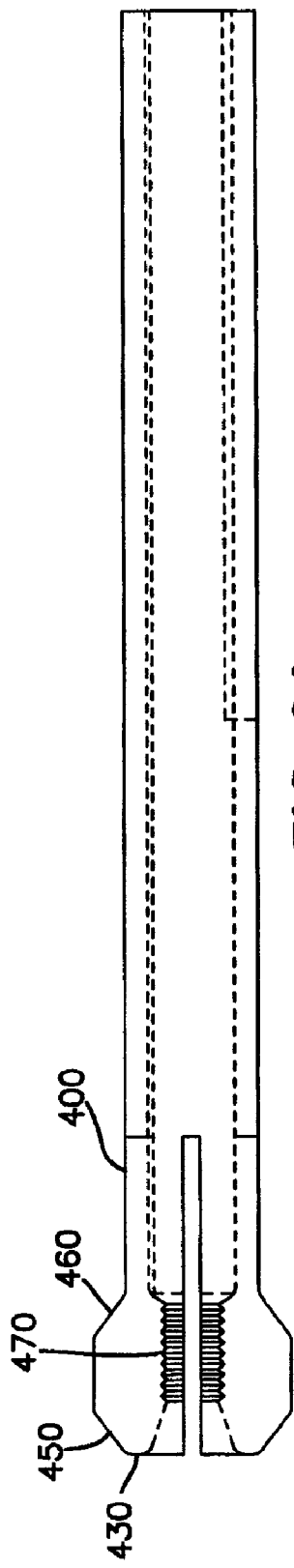
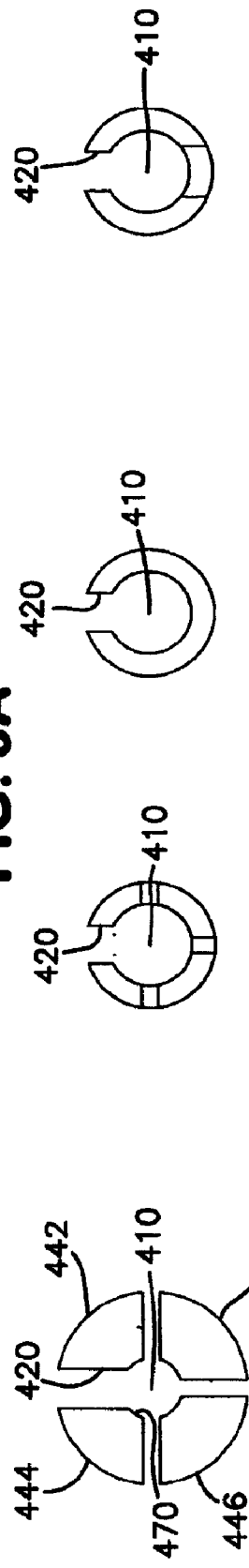

VASCULAR GUIDEWIRE CONTROL APPARATUS

CROSS-REFERENCE TO RELATED APPLICATIONS

This patent application claims priority benefit under 35 U.S.C. §119(e) of U.S. Provisional Patent Applications 60/757,443, filed Jan. 9, 2006, and 60/760,511, filed Jan. 21, 2006, and as a continuation-in-part under 35 U.S.C. §120 of U.S. patent applications Ser. No. 11/090,574 now U.S. Pat. No. 7,615,032 and Ser. No. 11/090,588 now abandoned, filed Mar. 24, 2005, the contents of which provisional and non-provisional applications are incorporated herein by reference in their entirety.

FIELD OF THE INVENTION

The present invention relates in general to the field of medical devices and, in particular, to devices for use in interventional and diagnostic access, manipulation within, and negotiation of, the vascular system.

BACKGROUND OF THE INVENTION

The vascular field of medicine relates to the diagnosis, management and treatment of diseases affecting the arteries and veins. Even when healthy, the anatomy of these vessels is complex, with numerous divisions leading into progressively smaller branches. Development of disease within these vessels often complicates matters by altering their caliber, flexibility, and direction. The interior, or lumen, of a blood vessel may develop constrictions, known as stenoses, and at times may even be obstructed, as a result of the development of atherosclerotic plaques or by the occurrence of tears or lacerations in the vessel wall, known as dissections. These obstructions may complicate the vascular anatomy by leading to the formation of new collateral pathways that establish new routes around the obstructions in order to provide blood flow down-stream from the blockage.

In order to diagnose and treat vascular diseases, a physician may in many instances perform a diagnostic or interventional angiogram. An angiogram is a specialized form of X-ray imaging, requiring physical access into a vessel with some form of sheath, needle or guide in order to allow a contrast dye to be injected into the vasculature while X-rays are transmitted through the tissue to obtain an image. The contrast dye illuminates the interior of the vessels and allows the physician to observe the anatomy, as well as any narrowings, abnormalities or blockages within the vessels. At times, more selective angiograms are used to delineate a particular area of concern or disease with greater clarity. Access to these more selective areas often requires the insertion of guidewires and guide catheters into the vessels.

Vascular guidewires and guide catheters can be visualized from outside the body, even as they are manipulated through the body's vascular system, through the use of continuous low-dose fluoroscopy. The negotiation of the complex vascular anatomy, even when healthy, can be difficult, time consuming and frustrating. When narrowed or obstructed by disease, the vessels are even more difficult—and sometimes impossible—to negotiate.

Attempts to address and overcome the difficulty of negotiating vascular anatomy have led to various devices, primarily guidewires and guide catheters, for assisting physicians. The devices vary in shape, diameter and length. In order to negotiate the smaller blood vessels as well as to provide some standardization within the industry, for example, many catheterization systems are sized to cooperate with guidewire diameters of 0.035" or less (0.018" and 0.014" being the next most common sizes).

The tips of these devices may be pre-formed into any of a variety of shapes to help negotiate obstacles or turns within the vasculature having particular geometries. For example, if the tip of a straight guidewire cannot be turned into the opening of a branch vessel, a guiding catheter with a tip having a 30 degree angle may be placed coaxially over the guidewire and used to point the tip of the wire into the appropriate orifice. Once the wire is in place, the catheter can be removed and the wire advanced further until the next obstacle is encountered at which time the guiding catheter is re-advanced into position.

A distinct disadvantage of these pre-formed devices is a need to constantly exchange and substitute different devices throughout the procedure. Changing of devices generally requires either that a catheter be withdrawn from the vasculature, while the collocated guidewire remains in position, and then be fully disengaged from the stationary guidewire; or, alternatively, that a guidewire be removed while the catheter remains in place, and substituted with a different guidewire. This exchange is not only time-consuming, but can also be dangerous: repetitive passage of these instruments within the vasculature can injure a vessel wall or release an embolic particle into the bloodstream that could lead to stroke, loss of limb, or even death. In an attempt to address and overcome these problems, catheters and guidewires have been developed to allow a practitioner to control, or at least to alter, the tip of the device in a more direct fashion. By means of an external control, the tip of the wire or catheter is turned, bent, flexed or curved.

Two types of approaches are currently used to impart the control of the wire/catheter tip: (1) direct mechanical linkage and (2) shape memory alloys (SMAs). The direct mechanical linkage approach employs actuators (e.g., wires, tubing, ribbons, etc.) that extend the full length of the guidewire/catheter. Manipulating the external, proximal portion of the control actuator, displaces the distal, internal portion of the wire. Specifically, the direct mechanical linkage can be disadvantageous in that when it is activated to deflect a guidewire's tip, it can impart a stiffening, shape-altering, performance-limiting constraint on the guidewire as a whole, thereby limiting its functionality.

The SMA approach involves use of alloys that are typically of metals having a Nickel-Titanium component (e.g., Nitinol) that can be trained in the manufacturing process to assume certain shapes or configurations at specific temperatures. As the temperature of a shape memory alloy changes, the structure of the material changes between states and the shape is altered in a predetermined fashion. SMAs are used extensively in the medical field for a variety of purposes, e.g., stents, catheters, guidewires. Typically, the material is trained to assume a specific configuration on warming (e.g., stents) or to return to its predetermined shape after deformation (e.g., Nitinol guidewires.).

If manufactured in a specific fashion, SMAs demonstrate a negative coefficient of thermal expansion when heated and can be trained to shorten a specified amount of linear distance. By passing an electric current through the material, the material's electrical resistance produces an increase in the material's temperature, causing it to shorten. Upon cooling, the alloy returns to its previous length. This characteristic of shape memory alloys has been used to impart a deflection or alteration in the tip of a guidewire or catheter.

One approach involves an outer sheath, an inner core and several nitinol actuators disposed concentrically about the inner core. These actuators are controlled via an electrical connection with the core wire and conducting wires traveling in parallel with the core itself. A controlling device is attached at the proximal (practitioner) end of the wire. By manipulating the controlling device, such as a joystick, the distal wire tip can be displaced in multiple directions. Another approach provides an end-mounted control device, at the proximal end, having a box shape.

Another approach involves an array of microcircuits that control two nitinol actuators that slide on an eccentric board with a low coefficient of friction. By altering the amount of actuator that is activated, a more or less bidirectional deflection can be imparted in the guidewire tip. As with the previous example, this device is also controlled by an end-mounted control device.

SUMMARY OF THE INVENTION

The apparatus, methods and systems according to the present invention, in their various aspects, address any of a range of problems associated with the manipulation of catheters and guidewires within vascular systems during invasive diagnostic or interventional radiological procedures or in other fields requiring precisely controlled penetration of narrow passageways. Among other advantages, embodiments of the present invention provide controllers for variable control, steerable guidewires that may have one more of the following advantages: coaxial structure, over-the-wire catheter compatibility, remote controllability, variably deflectable tip, low profile guidewire, controllability by a detachable, side-entry, easily positioned, single-handedly manipulated, combination torque and guidewire tip control device, ergonomic controllability from a position adjacent to the point of entry into the vasculature (or other passageway being accessed), and economical manufacturability. Aspects of the present invention also encompass or facilitate a reduction, or minimization, of the number of guidewire or guide-catheter exchanges necessary to accomplish a designated task or procedure, yielding an advantage not only in terms of the saving of time and other resources, but more importantly in reducing trauma to the passageways in which the guidewire is deployed. The combination of guidewire and controller according to aspects of the present invention allow convenient side-entry and single-handed repositioning of the controller along the length of the guidewire to allow the practitioner to manipulate the guidewire tip at any location along the guidewire, including at or near the point of entry, thereby improving ergonomics, control, efficiency, and ultimately, for medical guidewires, patient safety.

When used in the field of interventional radiology, the apparatus, systems and methods according to the present invention provide a solution in the form of an economical, completely coaxial, variable tip, low-profile guidewire remotely controlled by a detachable, easily positioned, single-handedly manipulated, combination torque and guidewire tip control device (controller). This device, with which embodiments of the controller according to the present invention may be used, overcomes shortcomings of prior vascular guidewire devices which lack the combination of a fully variable tip, a coaxial wire allowing compatibility with other devices, and a remote control system. Its dual utilization of the outer wrapped wire as a conducting element and structural support enables final low-profile design measurements that permit this system to be used with standard, currently available over-the-wire devices (e.g., stents, angioplasty balloons, and endo-grafts). The variable and controllable nature of the guidewire tip enhances the user's ability to manipulate the guidewire through difficult anatomy. Therefore, it minimizes the number of guidewire or catheter exchanges necessary to accomplish a designated task or procedure.

In one embodiment, a vascular guidewire and control system according to the present invention is a compact, coaxial, remotely and electrically controllable, variable tip guidewire that is fully exchangeable and compatible with most interventional catheter based devices.

A controller according to another aspect of the present invention provides a side-entry torque device compatible with the steerable guidewire according to the present invention, permitting single-handed repositioning of the controller along the guidewire, while reducing or minimizing trauma to the guidewire's electrical conducting wires. In addition to meeting criteria for the strength of the grip the controller applies to the guidewire, it offers several additional advantages. According to one aspect of the invention, the controller is provided with a switch that can be operated by the user to energize the steerable tip at the distal end of the guidewire to which the controller is affixed. This arrangement (among others according to the invention, discussed below), permits repositioning of the guidewire, by axial displacement, rotation and tip deflection, by the practitioner using a single hand. According to another aspect, the controller includes a fully detached collet adapted to engage with the body of the controller and a cap of the controller in order that the collet grip the guidewire with a uniform distribution of inwardly radial force. That is, the load each prong or face of the collet, of which there may be two or more, applies to the guidewire is uniformly distributed in a direction parallel to the axis of the guidewire, thereby reducing or minimizing the possibility of damage to the guidewire in the region where it is being gripped by the controller.

In an embodiment of another aspect of the present invention, the controller can easily be attached or detached and moved freely along the surface of the guidewire, which in turn allows a completely coaxial guidewire structure. In addition, the coaxial guidewire structure permits its unhindered use within existing types of catheters, sheaths and vessels. In other words, the guidewire can be made to be free of any permanent, designated attachment sites along its length. Thus, when the controller is removed, the guidewire has an unhindered, low-profile state with a uniform design diameter extending from the distal guidewire tip to the proximal guidewire end. The substantially uniform diameter guidewire configuration in an embodiment of an aspect of the present invention enables easy exchangeability with other guidewires and catheters, since catheters, sheaths, balloons or other devices can be readily slid over, or removed from, the guidewire.

In an embodiment of yet another aspect of the present invention, a controller, referred to above, comprises a combined torque and variable control device, which allows precise control of a guidewire tip, while retaining an ability to reposition and manipulate the guidewire in a mechanically advantageous position near the guidewire entry site into the sheath or catheter. As described above, the controller's easy attachment or removal at the closest possible point to the variable tip of the guidewire provides greater controllability of the tip. An embodiment of the invention permits flexible coupling of the controller to the guidewire, precise guidewire control, as well as a uniform diameter, purely coaxial guidewire system.

In an embodiment of a further aspect of the present invention, a guidewire controller comprises a guidewire torque control device combined with a switch, preferably of ergonomic design, for energizing the deflectable catheter tip. This combination permits the controller to be used to torque the guidewire, and to deflect or relax the guidewire tip, single-handedly. This combined configuration allows a precise manual guidewire control, aided by the tactile feedback of the distal guidewire tip, to help negotiate difficult anatomy or obstacles.

In an embodiment of another aspect of the present invention, a controller for facilitating manual control by a user of a guidewire comprises a housing having a primary axis and a first engagement feature substantially along the primary axis, a second engagement feature, non-parallel to the first engagement feature adapted to receive the guidewire, and a third engagement feature parallel with the first engagement feature for accommodating a portion of the guidewire. One or more of the engagement features may comprise slots. Furthermore, the second engagement feature may be perpendicular to the first engagement feature.

The invention, in yet another embodiment, provides a switch coupled to an electrical circuit causing the flow of electricity to the tip of a guidewire, wherein the switch may be held and/or manipulated by the user in conjunction with a controller for the guidewire in a single hand.

In an embodiment of another of its aspects, the invention provides a method of using a controller to displace, rotate, or deflect the tip of a guidewire using a single hand, comprising the steps of aligning a non-parallel engagement feature with the guidewire so that the controller is in a first position, engaging the guidewire with the non-parallel engaging feature, and shifting the controller to a second position in which the guidewire is fully received by the controller. The first position may or may not be perpendicular to the second position.

The various aspects of the present invention can be used in concert with guidewires, energizers, switches and according to methods that are the subject of co-pending applications entitled: Vascular Guidewire System, U.S. application Ser. No. 11/090,589; Energizer for Vascular Guidewire, U.S. application Ser. No. 11/090,588; Method for Use of Vascular Guidewire, U.S. application Ser. No. 11/090,512; and Vascular Guidewire Control Apparatus, U.S. application Ser. No. 11/090,574; all filed on Mar. 24, 2005, the contents of which are incorporated herein by reference in their entirety.

BRIEF DESCRIPTION OF THE DRAWINGS

FIGS. 1A-1F show aspects of an embodiment of a guidewire according to the present invention.

FIGS. 2A-2G show aspects of an embodiment of a guidewire controller in accordance with the present invention.

FIGS. 3A-3D show aspects of an embodiment of a guidewire power source or energizer according to the present invention.

FIG. 4 shows aspects of a second embodiment of a guidewire controller according to the present invention.

FIGS. 5A-5C show more detail of aspects of the embodiment of the controller shown in FIG. 4.

FIGS. 8A-8C show a controller assembly in an embodiment of the present invention including a shaft or housing portion according to the embodiment shown in FIGS. 6A-6B, a cap portion according to the embodiment shown in FIGS. 7A-7C and a collet portion according to the embodiment shown in FIGS. 9A-9E.

FIGS. 9A-9E show a collet portion of a second embodiment of a guidewire controller according to the present invention.

DETAILED DESCRIPTION

Figure 1D:
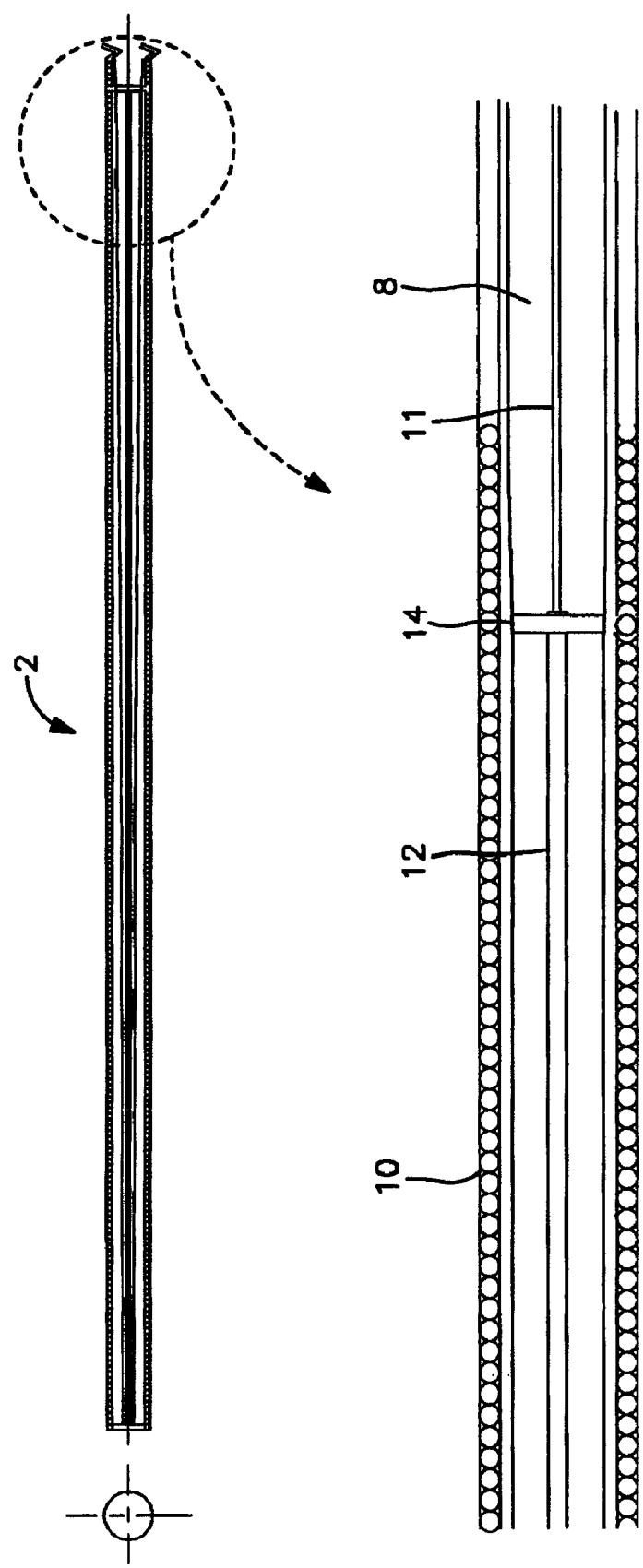
Figure 1E:
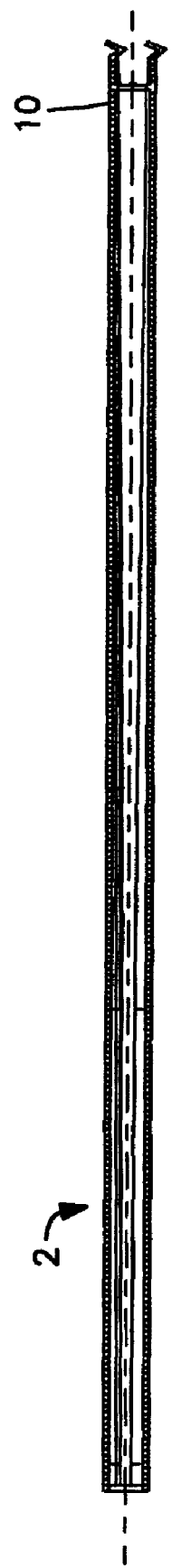

FIGS. 1A-1F show various views of an embodiment of a guidewire 1 according to the present invention. Guidewire 1, shown fragmented in FIG. 1A to permit the entirety of the guidewire to be shown in one figure, comprises three main sections. Guidewire 1 includes an elongate, tubular structure, having a proximal end 6 (see FIG. 1F) which resides exterior to the body of a patient (or other passageway with which guidewire 1 is being used) and physically handled by a practitioner, and a distal end, which in use will be within the passageway, having an actuator portion 2. The actuator portion 2 at a most distal portion of the guidewire 1 comprises a shape memory alloy (SMA) 12 or other suitable component adapted to introduce a deflection in a tip of guidewire 1, when activated. A third, central or mid-portion 4 of guidewire 1 is that section of the guidewire 1 between, and coupling, the distal and proximal portions and contains an inner, centrally disposed, electrically insulated, conductive wire 8. This wire, according to an aspect of the present invention, may be provided with a gradually tapered diameter as it progresses toward the distal tip of the guidewire. In the presently illustrated embodiment, the proximal end 6 of the guidewire 1 demonstrates where the inner wire 8 extends beyond the outer wrapped wire 10 and is exposed so as to be available for electrical connection to the controller device 46 and 150 as described below and illustrated in the accompanying figures.

FIG. 1A includes a more focused view of the mid-portion 4 of the guidewire 1 in an embodiment of an aspect of the present invention. The inner core wire 8 is a centrally disposed, electrically insulated, conductive wire having a gradually tapered diameter as it progresses toward the distal tip of the guidewire. Electrical insulation for the inner core wire 8 can be any of a variety of different suitable materials, but, in an embodiment of this aspect of the present invention, the insulation is preferably provided with a very low profile to accommodate the small diameter of the guidewire 1. In one embodiment, the insulation may be of a paralyene or polyamide coating of the type often used in medical indications. In another, an enamel coating similar to that used on magnet-wire could be used, as could other suitable materials.

In another aspect of the present invention, core wire 8 eventually tapers from a cross-section dimension that almost entirely fills the lumen of the outer wrapped wire 10 near the proximal end 6 of the wire to an appreciably smaller diameter as it progresses toward the distal end. Core wire 8, however, in this embodiment, may not necessarily extend to the most distal extent of the outer wrapped wire 10. Moreover, the full extent of the inner wire 8, its tapering characteristics and the selection of its composition can be varied to form embodiments exhibiting differing mechanical behavior at the tip of the guidewire 1, including but not limited to the magnitude and speed of deflection, stiffness, resiliency, and other characteristics. Some candidates for core wire 8 include, without limitation: NiTi based wires or steel musical wires with variable material characteristics of elasticity, resilience and ductility.

In an embodiment of one aspect of the present invention, the outer wrapped wire 10 serves dual functions. First, it provides a support layer which happens to be on the exterior of the guidewire 1. In this capacity, it provides mechanical structure sufficient for the wire to provide pushability, torquability and flexibility for proper use. In this embodiment, the outer wrapped wire 10 is constructed of a single filament wire, capable of electrical conduction, yet insulated in a similar fashion to the inner core wire 8. In one embodiment, the filament is a 304v stainless steel filament with a paralyene or similar insulating coating. In another embodiment, the filament is an approximately 34 to 36 AWG tin or copper wire, with an enamel insulating cover. Other suitable filaments, with or without coatings, may also be appropriate.

When in a helical configuration according to one aspect of the present invention, the outer wrapped wire 10 forms a tubular structure having a hollow lumen arising from its being wrapped/coiled in a tight, uniform diameter, helical fashion. In one example, outer wrapped wire 10 is sufficiently tightly coiled to possess a final maximal diameter less than or equal to about 0.035". Other arrangements of the outer wrapped wire 10, whether modified helical or non-helical arrangements, or even if tubular, woven or of other outer surface layer configuration, are also possible and within the scope of the present invention. Regardless of the precise wrapping configuration, the outer wrapped wire 10 in one embodiment extends from the most distal extent of the guidewire almost to the proximal portion of the guidewire.

Secondly, the outer wrapped wire 10 in an embodiment of an aspect of the present invention serves as an electrical path (e.g., return) for the actuator 12. The outer wrapped wire 10 forms an electrical connection with the distal end of actuator 12 at the end cap 18 as described below. Being electrically insulated, as described above, outer wrapped wire 10 remains electrically separated from the actuator 12 and the inner core wire 8, preventing short circuiting. At or near a proximal attachment site 14 of actuator 12, described below, the insulation of the outer wrapped wire 10 is selectively removed, exposing an electrically conductive portion of this wire 10. The outer surface of this insulation can be selectively removed in the manufacturing process by direct abrasion, chemical dissolution or other suitable process. The result of such process is an electrically conductive exposed surface, that nevertheless maintains electrical separation from any inner structures.

In another embodiment, the connection points of the actuator 12 could be reversed, such that the proximal attachment site 14 connects the outer wrapped wire 10 with the proximal end of actuator 12 while the distal end of actuator 12 is connected to the inner core wire 8. The described embodiment provides an actuator 12 that is straight when in a resting, unactuated state. This arrangement accommodates insertion and navigation of the guidewire 1 through the vasculature to a point where the sort of precise control enabled by the various aspects of the present invention can be deployed. In an alternative embodiment, not shown, that is also within the scope of the present invention, the actuator 12 could be in a non-straight or flexed condition when in a resting or non-energized state, and then return to a straightened position as the actuator 12 is energized by the user.

Figure 1F:
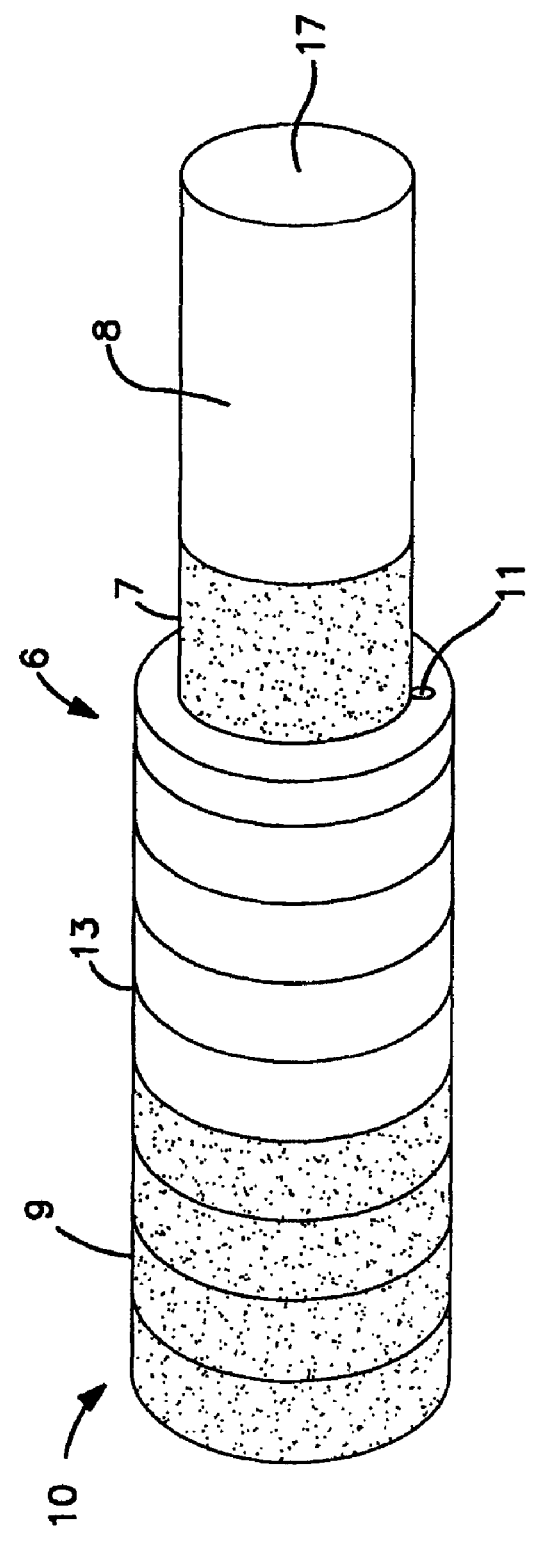

In another embodiment, shown in FIG. 1F, the guidewire 1 includes an inner core wire 8 (which, per FIGS. 1A-1C is connected at its distal end with the actuator 12) as well as a separate inner conducting wire 11. Inner conducting wire 11 is distinct from the inner core wire 8 and connects the proximal end of the actuator 12 to the proximal end of the outer wrapped wire 10, effectively bypassing a portion of the outer wrapped wire 10 in order to provide a decreased electrical resistance for the guidewire and actuator assembly. At the proximal portion 6 of the guidewire 1, this inner conducting wire 11 may be attached (e.g., without limitation, via soldering) or otherwise placed in direct or indirect electrical communication with the outer wrapped wire 10, such that a complete electrical connection can be made at the proximal portion 6 of the guidewire 1, e.g., at the proximal tip 17, via the energizer and switch.

FIG. 1F shows the extension of inner core wire 8 beyond the most proximal portion of the outer wrapped wire 10, in an embodiment of an aspect of the present invention. The exposed inner wire 8, with its insulation removed at this location, facilitates attachment of an electrical contact 20, such as an alligator clip, of a controller (described below) in order to complete an electrical circuit for the guidewire tip actuator 12. Outer wire 10 includes insulation 9 that is removed in a proximal portion 11. In use, the portion labeled 13, uninsulated, would serve as an electrically negative (or positive) connection point, while the uninsulated portion of the exposed inner core wire 8, to which the reference numeral is directed in FIG. 1F, would serve as an electrically positive (or negative) connection point.

FIGS. 1B and 1C show, among other features, the variable tip portion of the guidewire 1 in an embodiment of the present invention. The actuator 12 is a portion of the guidewire 1 that provides a mechanical force for deflecting the distal tip 2 of the guidewire 1. In this embodiment, actuator 12 comprises a fine wire constructed of a shape memory alloy (SMA). These alloys, as discussed above, most typically consist of a nickel-titanium (NiTi) based metal wire having a negative coefficient of thermal expansion, but may consist of different alloys. When heated, these alloys may contract a certain percentage of their overall length. Being electrically conductive, but having a comparatively high electrical resistance, they become heated when an electrical current passes through them and so contract linearly. When an applied current is switched off, the alloy cools and returns to its prior length. Typically, an alloy of this sort can tolerate thousands of repeated contraction and expansion cycles. In addition, SMAs are available in various diameters, lengths, surface coatings and characteristics. In one embodiment, a guidewire actuator 12 according to the present invention comprises a wire of SMA having a diameter of about 0.004". Other dimensions are possible and may be selected for particular guidewire characteristics. By altering the actual length and diameter of the actuator 12, different tip deflections can be configured to meet specific clinical situations.

FIG. 1D demonstrates an overall view of the distal tip 2 with an enlarged view of its proximal portion in an embodiment of an aspect of the present invention showing the actuator's proximal attachment site 14. The insulation on the inner core wire 8 is removed at this attachment site to provide an electrical contact with the actuator 12. The surface coating of the proximal actuator 12 is also removed to improve the connection. NiTi—and possibly other SMA-based wires may be difficult to attach via standard solder/weld methods and appear to be best connected via a mechanical means such as crimping or tying. In an embodiment of this sort, a fine mechanical crimp may be applied to attach the actuator to the inner core wire. An alternative embodiment would involve creating a divot in the inner core wire 8, about which the actuator 12 could be knotted. In yet another embodiment, a spot weld or conductive epoxy would fix the wire 8 at this site. Various methods for attaching actuators 12 to inner core wires 8, outer wrapped wire 10 or inner conducting wire 11, may provide a suitable a mechanical and electrical connection between the components of the guidewire 1.

In an embodiment of another aspect of the present invention, referring again to FIGS. 1B and 1C, the distal end of the actuator 12 is mechanically and electrically coupled at its distal attachment site 16 to the outer wrapped wire 10 in an eccentric (i.e., off-center) fashion. As shown in FIG. 1B, actuator 12 progresses from a central location 15 on the inner core wire 8 at its proximal attachment site 14, to an eccentric location at its distal attachment site 16 to the distal outer wrapped wire 10. This slight offset facilitates a mechanical advantage by which the actuator 12 can impart a deflection in the distal tip 2 of the guidewire 1. At the point of connection 16 between the outer wrapped wire 10 and the actuator 12, the insulation is removed from the outer wrapped wire to facilitate the electrical connection with the actuator 12. The mechanical connection is accomplished by crimping/compressing the actuator 12 to the outer wrapped wire 10 with the end cap 18 (shown in FIG. 1A). Alternative means of connection as listed above for the proximal attachment site could also apply to the distal attachment site.

FIGS. 2A-2G depict various views of a variable tip guidewire control mechanism (controller) 46 in an embodiment of another aspect of the present invention. The illustrated embodiment of the controller 46 provides a self-contained, dual purpose device capable of controlling the deflection of the guidewire tip 2 while also serving as a torque controller. In addition, as described below, the controller can be placed or repositioned anywhere along the length of the proximal end of the guidewire 1 to permit control of the axial progression or withdrawal of the guidewire 1. Controller 46 thus enables direct, inline, single-handed, fingertip control of the guidewire 1 at any point along the proximal portion of the guidewire 1 and external to the object, or medical subject, undergoing a procedure with the guidewire 1.

FIG. 2A provides a plan view of controller 46 and FIGS. 2B and 2C-2F side and end sectional views, which are exploded views to detail the interior of the device. The long axis of the controller 46 runs parallel with and is adapted to receive the guidewire 1 in a lateral fashion. When the controller 46 is in use, the guidewire 1 is seated in the guidewire channel 22. Guidewire channel 22 runs the full length of the controller 46 and its diameter is commensurate with the diameter of the guidewire 1 being used to permit an effective mating fit of the guidewire 1 within the controller 46, as elaborated upon below. With a latch 24 in an open position, access to the guidewire channel 22 is achieved via slot 26. This slot 26 extends the full length of the controller 46, with the exception of the region of a grasper swing door 28. The grasper swing door 28 is mounted via hinges 30 and fastened in a closed position by latch 24. With the guidewire 1 seated in place in the guidewire channel 22, the grasper swing door 28 can be placed in a closed position. In the closed position, a grasper mechanism 32 is placed firmly in contact with the guidewire 1, to permit torquing or linearly loading the guidewire 1.

As seen in FIG. 2G, the grasper mechanism 32 includes a set of metal prongs 34, e.g., without limitation, three in this embodiment, which may be of any suitable material, including but not limited to copper, brass, steel or other suitable electrically conductive material (if it is to provide an electrical connection in accordance with an aspect of the invention in the presently illustrated embodiment). In other embodiments where the actuator 12 will be energized by other means, the prongs may be of plastic, resinous or other suitable non-electrically conductive material. The prongs 34 may be positioned in order to circumferentially surround the guidewire 1 and thereby allow firm contact and grasping of the guidewire 1. Prongs 34 may be buttressed at their respective bases 52, such that they protrude slightly into the lumen of the guidewire channel 22. Therefore, when the grasper swing door 28 is closed, the prongs 34 are urged into contact with the guidewire 1. This arrangement serves two key functions. By firmly grasping the guidewire 1, controller 46 permits a torque to be applied to the guidewire 1 surface allowing the guidewire tip 2 to be rotated through 360 degrees in order to facilitate negotiation of obstacles. Additionally, the positioning of a grasper mechanism prong 34 at a 12:00 position on guidewire 1 facilitates an electrical connection with the exposed surface of outer wrapped wire 10. Thus, when slide switch 36 is moved forward by the user, switch contact 38 on the switch 36 touches contact 40, which is connected to the 12:00 grasper prong 34. The slide switch contact 38 is in electrical communication with the positive pole of battery 42 via an insulated, flexible wire 44. The negative pole of battery 42 is then connected to the attachment wire 48. The attachment wire 48 then extends from the controller 46 as a flexible external wire connected to attachment device 20 (such as an alligator clip). This attachment device 20 may then be clipped or otherwise electrically and mechanically coupled to the exposed portion of inner core wire 8. The slide switch 36 is therefore the means for activating the deflection of the guidewire tip 2. When slid into the forward position, slide switch 36 causes a complete electrical connection to be set up between the battery 42 and the actuator 12.

FIG. 2G depicts a method for operation of a guidewire 1 system in an embodiment of another aspect of the present invention. The controller 46, described above, is a separate physical entity from the guidewire 1. The distal portion and then the body portion of the guidewire 1 are introduced into the vasculature (or other passage way, for non-vascular guidewires) at a point of entry 60 in any of the standard ways known to those familiar with these techniques. The guidewire 1 can be manipulated by itself without the need for the control mechanism according to the present invention until the user reaches a point where the guidewire 1 can not be further negotiated through the vasculature, either secondary to the nature of the native anatomy or due to a diseased state such as a stenosis or obstruction. At this point the user has the option of using the controller 46 according to the present invention. Referring to FIG. 2B, the controller's connection wire 48 is first attached to the exposed portion of the inner core wire 8 via attachment 20. The user can then attach the controller at any point along the guidewire 1 that is convenient. As discussed above, the side entry feature of the controller 46 enables a user attach and remove the controller 46 from the guidewire 1 without needing to do so coaxially.

In order to attach the controller 46 to the guidewire 1, the grasper swing door 28 is unlatched and placed in the open position. The controller 46 is then placed on the guidewire 1 by means of the side-entry feature provided by the slot 26. The slot 26 directs the guidewire 1 into the guidewire channel 22. The guidewire channel is formed proximal as well as distal to the grasper mechanism 32, ensuring that the guidewire 1 is adequately supported until the grasper swing door 28 is closed. When the user is satisfied with the location of the controller, the grasper swing door 28 is closed and latched by means of the latch 24. The guidewire 1 is now firmly grasped in position. When the user slides the switch 36 forward, the actuator is energized as described above. This energized state permits current to flow to, and through, the actuator 2, thereby imparting a deflection on the guidewire tip 2. The degree and ultimate configuration of the deflection depends on several factors, including: the duration of activation, power source characteristics, and design considerations of the guidewire tip 2 (e.g., the length and diameter of actuator 12 and length of inner core wire 8).

In an embodiment of another aspect of the present invention, by rotating an attached controller 46, while simultaneously energizing the actuator 12 (by moving switch 36 in an ON position), the user can manipulate the guidewire tip 2 through the anatomy or past an area of disease. The same can be done with alternative embodiments, including such as are described below. When the slide switch 36 is returned to its off position, the actuator 12 is de-energized, allowing the guidewire tip 2 to return to its original position. This procedure can be repeated for thousands of cycles. The controller 46 can easily be repositioned on the guidewire 1 by releasing the latch 24, sliding the controller to the desired position and then re-latching the grasper swing door 28 (or as otherwise permitted by the particular mechanical design of the detachable controller, including one or more configurations described below). When it is not needed, the controller 46 can be removed entirely from the guidewire 1 without difficulty.

In an alternative embodiment illustrated in FIG. 2A (shown in dashed lines) the power source 56 for the controller 46 can be housed in apparatus separate from the controller device 46.

Another aspect of the present invention concerns the profile of the distal tip of the actuator 12, which in an embodiment of this aspect of the present invention is tapered. A wide variety of profiles are possible, and may be selected among to arrive at configurations suitable for particular design criteria for the guidewire 1. The deflection characteristics of the distal end of the guidewire 1 can be altered by appropriate selection of the design parameters of the distal tapered portion of the inner core wire 8. See, for example, FIG. 1E. Narrowing the distal taper, for example, will generally impart a tighter curve radius. This design principle according to the present invention can be used for different guidewires 1 as well as for differing uses, such as for accessing the renal arteries versus the carotid arteries.

A set of profile geometries that have been considered, but without limitation, are set forth in the table below. Included are two predominant cross-sectional shapes, oval and D-shaped (here, semicircular), with a listing of widths, heights (for the oval profiles), cross-sectional areas and lengths.

| ACTUATOR TIP PROFILES | | | | |
|---|---|---|---|---|
| DIMENSIONS | WIDTH (INCHES) | HEIGHT (INCHES) | LENGTH (INCHES) | CROSS-SECTIONAL AREA (INCHES) |
| OVAL | | | | |
| 1 | 0.010 | 0.0039 | 0.25 | 3.9E−5 |
| 2 | 0.010 | 0.0039 | 0.5 | 3.9E−5 |
| D-SHAPED/SEMICIRCULAR | | | | |
| 1 | 0.008 | see width | 0.25 | 2.5E−5 |
| 2 | 0.10 | see width | 0.25 | 3.92E−5 |
| 3 | 0.008 | see width | 0.25 | 2.5E−5 |

In accordance with an aspect of the present invention, an actuator tip having a D-shaped cross-sectional profile advantageously permits onset of curvature of the tip in a preselected direction. Actuator tips having an asymmetrical cross section have a preferential direction of curvature when subjected to axial loading upon energizing of the actuator. D-shaped or semicircular cross sections tend to initiate curvature consistently about the flat side of the "D" or semicircle. Among other advantages, a profile having this general configuration will tend to repeatedly curve in the same direction, so that a user that happens to be holding the guidewire 1 in a particular orientation need not "recalibrate" with each energizing of the actuator 2.

Many alternative embodiments of the actuator 2 are within the scope of the present invention. In one example, an actuator wire 12 according to the present invention makes use of a pulley-type of mechanism, whereby an end of the actuator 2 is attached to the inner core wire 8 as before. The insulated wire 12 is then looped around the distal end of the outer wrapped wire 10, rather than being fixed at that location. Insulated wire 12 is then run in parallel to itself and attached more proximally 54 to the outer wrapped wire 10, as shown. This arrangement enables a doubling effect of the actuator force as it shortens over a given distance. A greater degree of force can then be used to impart different configurations on the guidewire tip 2 than might be possible in other embodiments of this aspect of the present invention.

FIGS. 2B-2F show an embodiment of a latch mechanism for controller 46 according to the present invention. This embodiment involves a compressive internal latch mechanism rather than an external latch as described above. This embodiment could offer improved single-handed operation of the controller 46 and guidewire 1. The latch is engaged in a simple manner by closing and squeezing the grasper swing door 28, that is, with guidewire 1 mounted in the controller 46. To release the latch, the door is compressed a second time, thereby releasing the hooking mechanism and allowing the grasper swing door 28 to open again.

In still another embodiment, FIG. 2G shows an integrated "all-in-one" system that does not require an external connection wire 48. The controller 46 uses the outer wrapped wire 10 in a similar fashion to the embodiment described above, while a second, pointed, penetrating contact point 58 on the controller penetrates in-between the coils of the outer wrapped wire and makes contact with the inner core wire 8. This contact is connected to the opposite pole of the battery by a wire. This would allow a complete electrical circuit to occur when the slide switch 36 is activated, thereby facilitating deflection of the guidewire tip.

Yet another embodiment of various aspects of the present invention is shown in FIG. 1D. As shown in the upper portion of Figure ID a fine inner conducting wire 11 is provided in coaxial location within the outer coil 10, permitting the electrical return current to be transmitted with less resistance, lowering the total power necessary to activate the actuator 12 at the distal end of the guidewire 1. This electrically insulated inner conducting wire 11 is electrically connected to the proximal end of the actuator 12 via an electrical connection that is insulated from the inner core wire 8. This inner conducting wire 11 tracks along the surface of the inner core wire 8 and is electrically coupled to the proximal end of the outer coil 10. The attachment of the proximal end of the wire 11 to the power source (not shown) can then still be made using the outer coil 10 as the conducting surface. This inner conducting wire 11 may be composed of a highly conductive material capable of transmitting a current with very little drop in resistance, despite its fine diameter. An example of this material, without limitation, would be a MP35N-DFT having a Silver core. A potentially suitable diameter, without limitation, would be in the range of 0.002". Both of the electrical connections of the guidewire 1 to the external power source can occur at the proximal end of the guidewire 1.

Another aspect of the present invention concerns an energizer and connection system 100 providing a mechanism for attaching the proximal portion of the guidewire 1 to a power source, the energizer 110. In order to obtain a completely coaxial system, the proximal portion or end of the guidewire 1 should preferably fall within design tolerances, e.g., diameter, for the remainder of the wire. This arrangement allows for therapeutic and diagnostic catheters and devices to be axially or coaxially mounted over the (free) proximal end and coaxially track over or ensheathe the guidewire 10. An embodiment of this aspect of the present invention is shown in FIGS. 3A-3D and FIG. 4. The proximal portion 6 of the guidewire 1 is formed of an outer wrapped wire 10, having a protruding inner core wire 8. The inner core wire 8 is electrically insulated from the outer core wire 10. The proximal tip 17 (as seen, e.g., in FIG. 1F) of the inner core wire 8 has little or no insulation, such that it may make electrical connection with a connection jack 120. The proximal portion of the outer wrapped wire 10 also lacks insulation, such that it may also make electrical contact with a different portion of the connection jack 120. Therefore, these two distinct connection points on the guidewire are able to make an electrical connection between the guidewire 1 and the connection jack 120 in order to allow delivery and return of electrical current while still meeting the design requirements of a low profile, coaxial system. Thus, this embodiment of a connection system 100 according to the present invention still employs the essential characteristics of the guidewire 1 described above, namely using of the inner core wire 8 and the outer coil wire 10. The inner conducting wire 11, in an embodiment of this aspect of the present invention, merely provides a more efficient transmission of power from the distal actuator 12 to the proximal end 17 of the outer coil 10.

An embodiment of another, related aspect of the present invention, a power source for activation of the guidewire 1 is shown in FIGS. 3A-3D. A controller 46 (or, per the description below, 150) provides improved tactile feedback and ease of manipulation of the guidewire 1 when it is as light as possible. Therefore, housing a battery-type power source within the housing of the controller 46 itself may not be preferred, though it is within the scope of the present invention. A power source or energizer 110, in an embodiment of an aspect of the present invention, may itself be separate from the controller 46 or 150 in a fashion similar to that described in the embodiment shown in FIG. 2A. The power source or energizer 110, shown in FIGS. A-3D, includes a connection jack 120 to accept the positive and negative terminals of the guidewire 1, a power source in the form of one or more batteries 130, and connecting wires that couple a detachable switch on the controller 46 or 150 to the power source or energizer 110.

In an embodiment of this aspect of the present invention, the connection jack 120 of this system allows insertion of a length of the proximal end 17 and a proximal portion of the guidewire 1 so that an electrical connection can be made between the outer core wire 10 and the inner core wire 8. Other arrangements are also possible, including but not limited to a distinct connector element adapted to mate with jack 120, but should preferably have an external diameter not substantially greater than a maximal diameter of the guidewire 1. The power source or energizer 110 also provides a means to mechanically grasp and stabilize the proximal portion or end 17 of the guidewire 1 during use. In an embodiment of this engagement mechanism 112 according to the present invention, the mechanism is slidably operable with a thumb or finger to releasably engage the proximal end or tip of the guidewire. The power source or energizer 110 is light enough such that as the guidewire 1 is advanced, the power source or energizer 110 is easily pulled with the guidewire 1. Or, the guidewire 1 may be looped around the power source or energizer 110 to build slack into the guidewire 1 and reduce or minimize the necessary movement of the power source or energizer 110. The power source or energizer may be provided with a recess or slot 124, or other suitable mechanism, for receiving a portion of the guidewire 1 in order to enhance stability of the guidewire 1 during its use. The power source of energizer 110 may also be provided with a mechanism 114 (which as shown may, but need not, be on the engagement mechanism 112) for temporarily gripping the proximal portion or end of the guidewire. The connection jack 120 also allows 360 degrees rotation of the guidewire 1 within the power source or energizer 110 to allow the user, via controller 46 or 150, to torque the guidewire 1 without limitation. The mechanical connection may occur in a variety of means including through the use of an electrically conductive gripping spring, socket or latch. This jack 120 is electrically connected to the power source or energizer 110. Based on the anticipated power requirements, the power source or energizer 110 may be varied. In one embodiment, two wires exit the energizer 110 and are connected via wire(s) 122 to the switch, e.g., 26 or 160. When the switch 36 or 160 is closed, electrical current flows from the battery, e.g., 130, through wire(s) 122 and the switch, e.g., 160, to the guidewire 1 with the resultant activation of the distal tip.

In another embodiment, the switch 160 may be configured to be attachable to the controller 150. The switch 160 may be of circumferential geometry, with a slot provided along one side. This slot is sized to accommodate the side-entry ability of the controller 150. The switch 160 could be placed over the guidewire 1 and then advanced onto the back end of the controller 150, where it would lock into position on the controller 150. When the switch 160 is not necessary for use of the guidewire 1 during a particular procedure, the switch 160 can be removed from the controller 46 and be placed or stored elsewhere. This removability, in this embodiment, may permit greater versatility of use. In various embodiments, the switch 160 may, for example, incorporate a rubberized, bladder type switch with two near-circumferential contacts. This embodiment, shown in FIGS. 4 and 5A-5C, allows a user to activate the switch 160 at any point on its circumference, providing the user with simple, ergonomic control of the switch 160.

In another embodiment of the switch 160, the switch 160 is not configured to be attachable to the controller 150. Rather, it is ergonomically designed to be separate from the controller 150 and held in the practitioner's hand in conjunction with, but separate from, the controller. This still allows single-handed control of the distal tip of the guidewire 1.

Figure 11A:
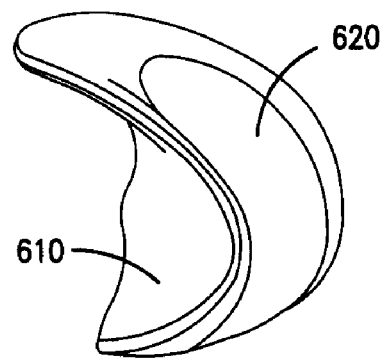
FIGS. 11A-B show aspects of an embodiment of a switch used in conjunction with a guidewire controller according to the present invention.
Figure 11B:
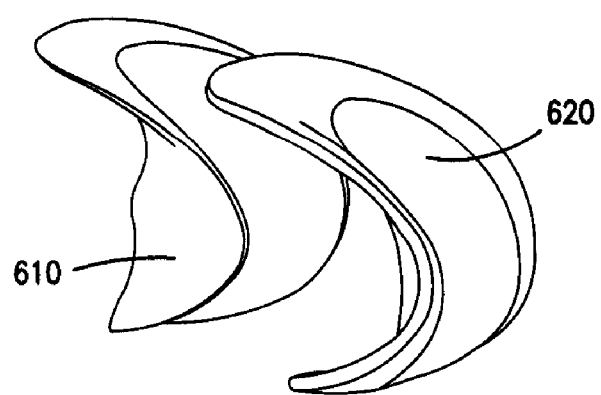

In another embodiment, shown in FIGS. 11A-B, the switch can be designed to sit in the user's hand while being held by, for example, just the fourth and fifth fingers, or even a single finger. According to this embodiment, the switch may be composed of a polymer or elastic material known or used in the art, and may consist of two halves or portions as shown in FIG. 11B. Furthermore, as shown in FIG. 11A, the switch may have a curved surface 610 adapted for the contour of the user's fingers gripping the switch, and a related, convex surface 620 accommodated for the palm or portion of the user's hand adjacent to the fingers holding the switch. Thus, use of the fourth and fifth fingers to hold the switch according to this embodiment may include using part of the user's hand or palm as well. The switch may be activated by squeezing one or both of the surfaces 610 and 620 of the switch when it is placed in the user's hand as described above. Embedded electronics, not shown in these Figures, may be used to help accomplish such activation. These features of the switch allow the user to maintain simple, ergonomic control of the switch and single-handed control of the distal tip of the guidewire 1. In this embodiment, the switch may be separate from the controller 150, but used in conjunction with the controller 150 in a single handed fashion. Furthermore, the switch may be connected to energizer 110 by either a wired or wireless connection.

Figure 6A:
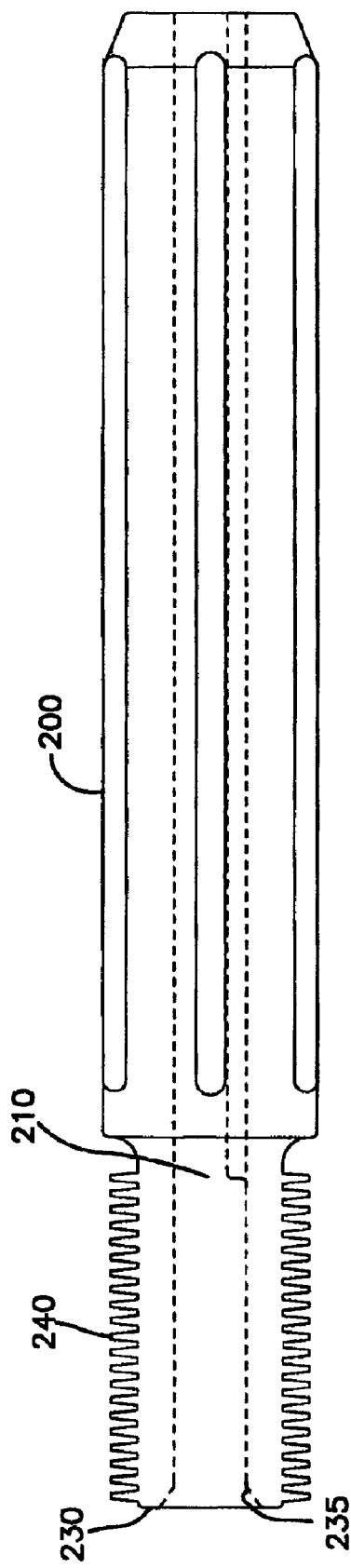
FIGS. 6A-6B show a shaft, body, or housing portion of a second embodiment of a guidewire controller according to the present invention.
Figure 6B:
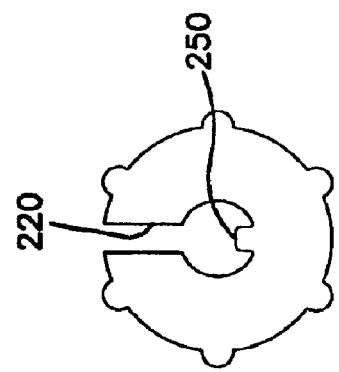
Figure 7A:
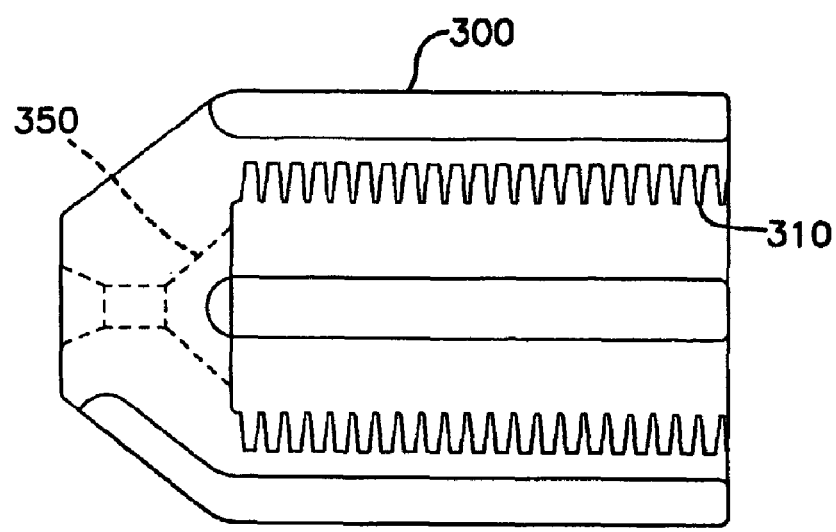
FIGS. 7A-7C show a cap portion of a second embodiment of a guidewire controller according to the present invention.
Figure 7B:
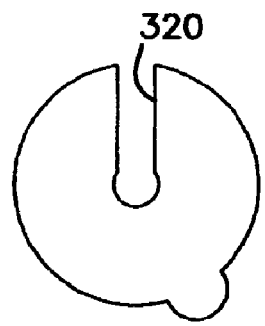
Figure 7C:
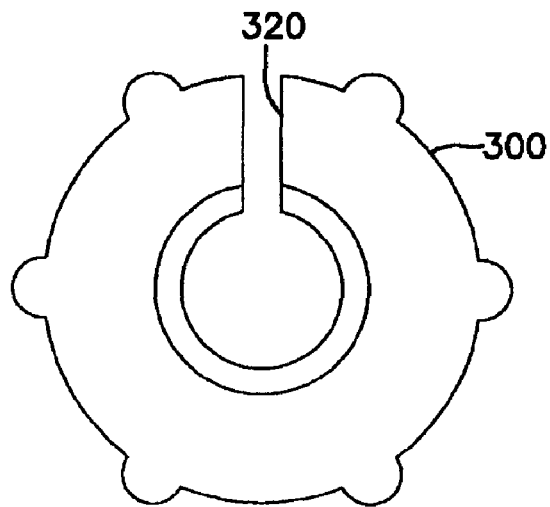

Another embodiment of the controller 150 according to the present invention is shown in FIGS. 4 and 5A-5C. This embodiment employs a side-entry slot mechanism, like the embodiment described above. Rather than the latch type closing mechanism disclosed in that example, however, this embodiment employs a screw-down collet configuration, which may permit a mechanical advantage relative to the illustrated latch-type mechanism. The controller 46 in this embodiment includes three components. The first, shown in FIGS. 6A and 6B, is a housing, body or shaft 200 having an inner lumen 210 and a side slot 220 along its length. The slot 220 allows for side-entry of the guidewire 1 into the shaft lumen 210. The distal end 230 of the shaft 200 is provided with external screw-threads 240 for adequate mechanical advantage when engaging a mating, internally threaded cap 300 having mating threads 310. The shaft 200 may be formed of any number of suitable materials including, without limitation, nylon-based, high grade medical plastics having a comparatively stiff modulus of elasticity.

Figure 10A:
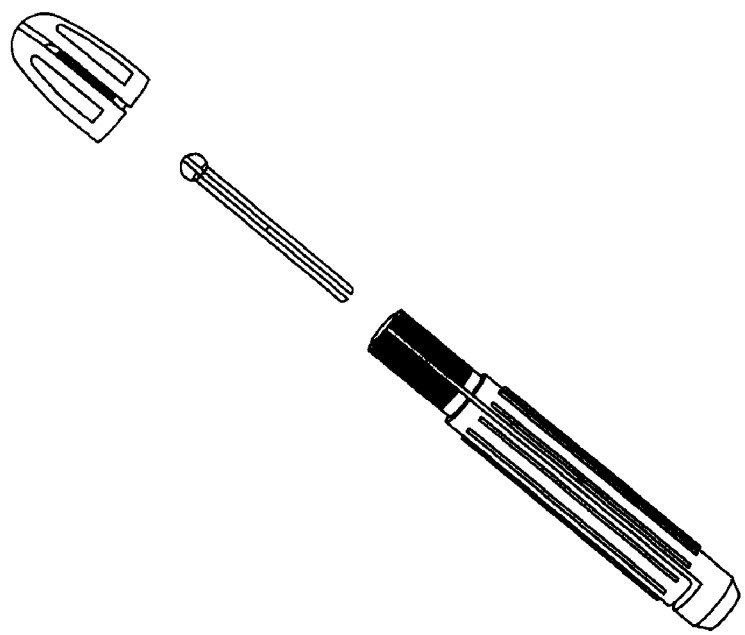
FIGS. 10A-B show aspects of an embodiment of a controller assembly including a shaft or housing portion having an engagement feature adapted to receive a guidewire along its side at a location near the point of entry.
Figure 10B:
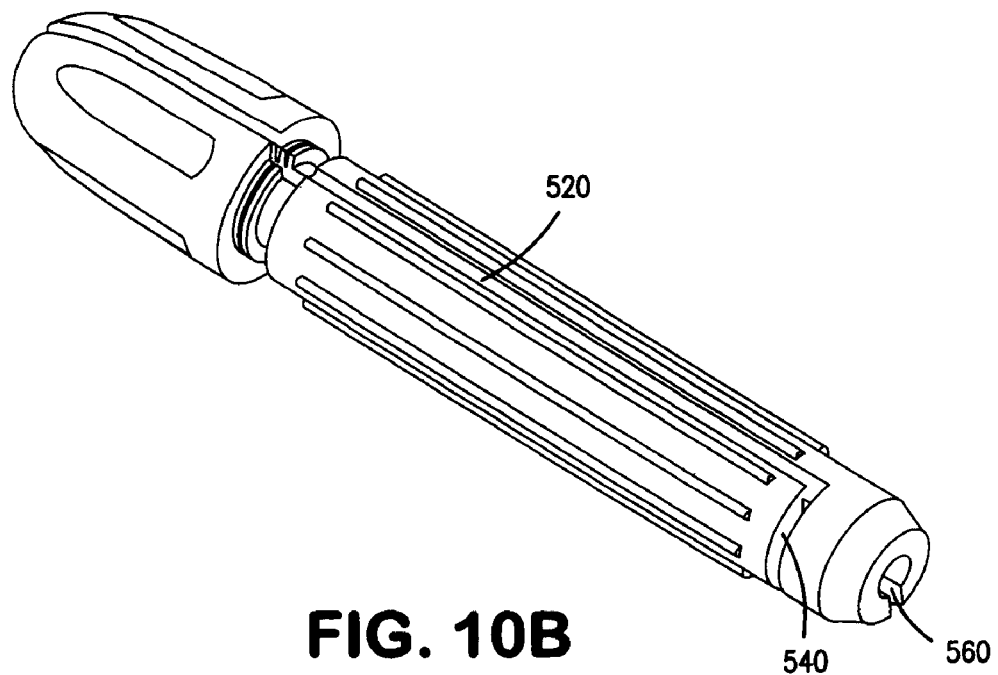

According to embodiments of aspects of the present invention, the controller 150 is provided with an engagement feature for enabling, or at least facilitating engagement of the guidewire 1 by the controller 150 using one hand only. In one embodiment, the single handed engagement feature is an engagement slot that is non-parallel to a primary receiving feature (e.g. slot 220) of the controller 150. FIG. 10B represents one possible depiction of this embodiment of an aspect of the invention, in which the engagement slot 540 is substantially perpendicular to the primary receiving slot 520. This depiction represents only one way of achieving the single handed engagement feature of the controller 150, as other arrangements of the engagement slot 540 and primary receiving slot 520 may also be utilized.

The side-entry slot mechanism or single handed engagement feature in this embodiment of the controller 150, or in the embodiments described above, may consist of a slot having three portions: a primary slot 520 parallel to the axis of the controller, a second, engagement slot 540, which may be non-parallel to the primary slot 520, for engaging the guidewire, and a third slot 560, parallel with the primary slot 520 and the controller 150, for accommodating a portion of the guidewire 1. As shown in FIG. 10, the primary slot 520 may receive a length of the guidewire 1 similar to slot 26 or 220 in the embodiments above. The engagement slot 540, perpendicular to the primary slot 520 in this illustrated embodiment, is continuous with the primary slot 520 and is similarly adapted to align with and receive a guidewire 1. Together, these portions of the slot may engage the guidewire 1. Using a single hand, the practitioner can first orient the controller 150 non-parallel to the guidewire 1 and place the engagement slot 540 over the side of the guidewire 1. Subsequently, the practitioner can align the primary elongate slot 520 such that it can slide over and finally sit on the guidewire 1. The practitioner may, during this procedure, maintain control of the guidewire 1 with the other hand, which remains free during engagement of the controller 150. The engagement slot 540 may function as a fulcrum that facilitates the act of aligning the primary slot 520 over the guidewire 1 and locking the controller 150 onto the guidewire 1. The "L" shape of the slot in this particular embodiment allows the practitioner to achieve such alignment and repositioning of the controller 150 in an efficient, single handed manner. Furthermore, the advantages of side entry and removal with respect to the guidewire are preserved.

The second component of the controller 150 is a collet 400, shown in FIGS. 8A-8C and 9A-9C. The collet 400 is configured to slide in an axial fashion within the lumen 210 of the shaft 200. The collet 400 is also provided with a side slot 420 to allow the guidewire 1 to pass within its lumen 410. On the opposite side of the slot 220 of shaft 200 is a spline 250 that fits within a groove on the inner surface of the shaft 200. Therefore, when the collet 400 is within the shaft 200, the collet 400 will not rotate, but will maintain an alignment of the slots 420 and 220, respectively, of the collet 400 and the shaft 200. The distal end 430 of the collet 400 includes at least two prongs. In the illustrated embodiment, but without limitation, the prongs 442, 444, 446, 448, of which there are 4, are formed as part of the collet 400, which slides within the lumen 210 of the shaft or housing 200. Therefore, as the cap 300 is tightened, it compresses the prongs 442, 444, 446, 448 on the front end radially inwardly toward the guidewire 1 in order to grip it. The cap 300 also drives the sliding collet 400 into the shaft 200 as it is tightened. The distal or leading end 230 of the shaft or housing 200 is provided with a reverse bevel 235 so that, as the collet 400 is driven into the shaft 200, the prongs 442, 444, 446, 448, which are provided with respective complementary bevels 437 at their proximal end, are also compressed by this bevel 235 of the shaft or housing 200. This bevel arrangement increases the mechanical advantage of the collet 200 and also allows the prongs 442, 444, 446, 448 to grip the guidewire 1 with a more evenly distributed gripping surface—rather than being gripped at only one point, which can rotate the prongs and cause them to impart undue and damaging point stresses on the guidewire 1 or its components. Distribution of the prongs 442, 444, 446, 448 around the lumen 410 permits their compression to impart a grip on the guidewire 1 when the cap 300 is tightened to engage the bevels 350 of the cap 300 and shaft 200 with the complementary bevels of the prongs 435 of the collet 400. A gripping surface 470 on each prong 442, 444, 446, 448 may be curved, concavely with respect to the guidewire 1, to disperse the compression forces of the respective prong 442, 444, 446, 448 along the surface of the guidewire 1. This dispersion reduces or eliminates a focused, high-pressure contact that could potentially damage underlying electrical components of the guidewire 1. Further, the shaft in this embodiment incorporates a means to lock the removable switch 160 in place.

A third component of the controller 150 is the cap 300, shown in FIGS. 5A, 7A-7C and 8A-8C. As shown in FIGS. 8A-8C, the cap 300 mates with the shaft 200. Inner threads 310 of the cap 300 allow for longitudinal motion of the cap 300 along the shaft 200. The cap 300 also is provided with a slot 320 that is aligned with the shaft slot 220 and collet slot 420 during insertion and removal of the guidewire 1. As the cap 300 is tightened, the inner bevel 350 of the cap 300 compresses the prongs 442, 444, 446, 448 of the collet 400 down and onto the guidewire 1. Furthermore, as the collet 400 is driven into the shaft 200, the proximal bevel 437 of the collet prongs 442, 444, 446, 448 abutting bevel 235 of the shaft 200 provide additional mechanical advantage to compress the prongs onto the guidewire 1. The cap 300 is constructed of any suitable material having a sufficiently stiff modulus of elasticity in order to prevent outward deflection of the cap 300 as it is tightened on the shaft 200.

The outer configuration of the shaft 200 incorporates a proximal tapered end that allows for advancement of the switch 160 from the back end and onto the controller 150. The switch 160 may snap into position (engaging with means 260) when desired.

An additional embodiment of the switch and connection system according to an aspect of the present invention may utilize a wireless system. In this wireless embodiment a transmitter within the switch is configured to transmit a signal to the power source or energizer 110 at the proximal end of the guidewire 1. When the power source or energizer 110 receives the signal, a circuit is closed within the power source or energizer 110, thereby allowing deflection to occur at the distal end of the guidewire 1. This wireless embodiment may incorporate a small scale wireless device, such as (but not limited to) a Zigbee or Bluetooth wireless protocol system, which permits the system to be implemented within the design constraints of the switch and connection system.

The various aspects of the present invention not only permit the use of a steerable or controllable guidewire having advantages over previous systems, but also allow the guidewire to be controlled at or near the point-of-access into the vasculature. The present invention also enables on-the-wire control while leaving the proximal end of the guidewire 1 to be selectably and easily freed to permit coaxial loading of other interventional radiology devices on the guidewire 1 (e.g., catheters, angioplasty balloons and other devices).

The various apparatuses and methods according to the present invention, and the principles that make them possible, may be applied in any fields requiring a steerable guidewire. Such fields include not only the vascular field of medicine, but also additional medical fields including, but not limited to, urology, general surgery and gynecology. Furthermore, these principles could also be applied to areas outside the medical field, such as veterinary medicine, inspection, mining, telecommunications (e.g., conduit), water distribution, security, national defense, electrical, entertainment and other systems.

While the various aspects of the present invention have been shown and described with reference to particular embodiments, persons skilled in the art will understand that various changes in form and details may be made without departing from the spirit and scope of the invention as set forth in the appended claims. The many details and specifics should not be construed as limitations on the scope of the invention as claimed, but rather as exemplifications, and the scope of the invention should be determined not by these illustrated embodiment(s), but rather by the appended claims and their legal equivalents.

What is claimed is:

1. A controller which facilitates manual control of a guidewire, said controller comprising:
    a housing having an outer side wall which extends around a passage, said passage extends between proximal and distal end portions of said housing,
    an engagement slot which extends between opposite side portions of said housing in a direction transverse to a longitudinal central axis of said passage, said engagement slot extends through said outer side wall of said housing to enable a portion of the guidewire positioned in said engagement slot to extend between opposite end portions of said engagement slot and to extend across said passage,
    a second slot extending from a first one of the end portions of said engagement slot to said distal end portion of said housing, said second slot extends through said outer side wall of said housing to enable a portion of the guidewire to move through said second slot into said passage,
    a third slot extending from a second one of the end portions of said engagement slot to said proximal end portion of said housing, said third slot extends through said outer side wall of said housing to enable a portion of the guidewire to move through said third slot into said passage, said second and third slots are disposed at opposite side portions of said housing, and
    a gripper at least partially disposed within and connected with said housing, said gripper having surfaces to grip a portion of the guidewire disposed in said passage, said gripper includes a gripper actuator connected with said housing and a gripper member having surfaces which are pressed against the guidewire under the influence of force transmitted from said gripper actuator to hold the guidewire against movement relative to said gripper member, said gripper member having a fourth slot which is aligned with one of said second and third slots to enable a portion of the guidewire to move through said one of said second and third slots and said fourth slot into said passage.

2. A controller as set forth in claim 1 wherein said gripper member is a collet and said gripper actuator is a cap which extends around a portion of said collet.

3. A controller as set forth in claim 2 wherein said gripper is at least partially disposed within and is connected with said distal end portion of said housing and said one of said second and third slots is said second slot.

4. A controller as set forth in claim 1 wherein said engagement slot has first and second parallel side surfaces which extend across said passage, said second slot has a third side surface which extends from an intersection with said first side surface of said engagement slot at the first end portion of said engagement slot to said distal end portion of said housing, said second slot has a fourth side surface which extends parallel to said third side surface of said second slot and extends from an intersection with said second side surface of said engagement slot at the first end portion of said engagement slot to said distal end portion of said housing, said third slot has a fifth side surface which extends from an intersection with said first side surface of said engagement slot at the second end portion of said engagement slot to said proximal end portion of said housing, said third slot has a sixth side surface which extends parallel to said fifth side surface of said third slot and extends from an intersection with said second side surface of said engagement slot at the second end portion of said engagement slot to said proximal end portion of said housing.

5. A controller a set forth in claim 1 wherein said second and third slots have linear longitudinal central axes which extend parallel to a longitudinal central axis of said passage.

6. A controller as set forth in claim 1 wherein a portion of the guidewire positioned in said engagement slot extends through a longitudinal central axis of said passage.

7. A controller as set forth in claim 1 wherein a longitudinal central axis of said passage has a linear configuration, said second and third slots have linear longitudinal central axes which extend parallel to the longitudinal central axis of said passage.

8. A controller as set forth in claim 7 wherein said engagement slot has a linear longitudinal central axis which extends perpendicular to and intersects the longitudinal central axes of said second and third slots.

9. A controller as set forth in claim 7 wherein said engagement slot has a linear longitudinal central axis which intersects the longitudinal central axis of said passage.

10. A controller as set forth in claim 1 wherein said gripper member is integrally formed as one piece with said housing, said gripper actuator is a cap which extends around one end portion of said gripper member.

11. A controller as set forth in claim 1 wherein said gripper member is formed separately from and is connected to said housing, said gripper actuator is a cap which extends around one end portion of said gripper member.

12. An apparatus for use with a guidewire, said apparatus comprising:
- a housing having an outer side wall which extends around a passage, said passage extends between proximal and distal end portions of said housing,
- an engagement slot which extends between opposite side portions of said housing in a direction transverse to a longitudinal central axis of said passage, said engagement slot has first and second parallel side surfaces which extend across said passage,
- a second slot extending from a first end portion of said engagement slot to said distal end portion of said housing in a direction parallel to the longitudinal central axis of said passage, said second slot has a third side surface which intersects said first side surface of said engagement slot at a first corner, said third side surface of said second slot extends from said first corner to said distal end portion of said housing in a direction parallel to the longitudinal central axis of said passage, said second slot has a fourth side surface which intersects said second side surface of said engagement slot at a second corner, said fourth side surface of said second slot extends from said second corner to said distal end portion of said housing in a direction parallel to the longitudinal central axis of said passage,
- a third slot extending from a second end portion of said engagement slot to said proximal end portion of said housing in a direction parallel to the longitudinal central axis of said passage, said third slot has a fifth side surface which intersects said first side surface of said engagement slot at a third corner, said fifth side surface of said third slot extends from said third corner to said proximal end portion of said housing in a direction parallel to the longitudinal central axis of said passage, said third slot has a sixth side surface which intersects said second side surface of said engagement slot at a fourth corner, said sixth side surface of said third slot extends from said fourth corner to said proximal end portion of said housing in a direction parallel to the longitudinal central axis of said passage, and
- a gripper connected with said housing, said gripper having surfaces to grip a portion of the guidewire disposed in said passage, said gripper includes a gripper actuator connected with said housing and a gripper member having surfaces which are pressed against the guidewire under the influence of force transmitted from said gripper actuator to hold the guidewire against movement relative to said gripper member, said gripper member having a fourth slot which is aligned with one of said second and third slots.

13. An apparatus as set forth in claim 12 wherein said gripper member is a collet and said gripper actuator is a cap which extends around a portion of said collet.

14. An apparatus as set forth in claim 12 wherein said gripper is at least partially disposed within and is connected with said distal end portion of said housing, said gripper having a fourth slot which is aligned with said second slot.

15. An apparatus as set forth in claim 12 wherein said third side surface of said second slot extends perpendicular to said first side surface of said engagement slot at said first corner, said fourth side surface of said second slot extends perpendicular to said second side surface of said engagement slot at said second corner, said fifth side surface of said third slot extends perpendicular to said first side surface of said engagement slot at said third corner, said sixth side surface of said third slot extends perpendicular to said second side surface of said engagement slot at said fourth corner.

16. An apparatus as set forth in claim 12 wherein said second and third slots have a linear configuration and extend parallel to a longitudinal central axis of said passage.

* * * * *